United States Patent
Hershey

(10) Patent No.: US 9,155,889 B2
(45) Date of Patent: Oct. 13, 2015

(54) METHODS AND APPARATUS FOR TREATING GLIOMA

(71) Applicant: BOSTON SCIENTIFIC NEUROMODULATION CORPORATION, Valencia, CA (US)

(72) Inventor: Bradley L. Hershey, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/309,811

(22) Filed: Jun. 19, 2014

(65) Prior Publication Data

US 2014/0379060 A1 Dec. 25, 2014

Related U.S. Application Data

(60) Provisional application No. 61/838,059, filed on Jun. 21, 2013.

(51) Int. Cl.
*A61N 1/00* (2006.01)
*A61N 1/36* (2006.01)
*A61N 1/05* (2006.01)

(52) U.S. Cl.
CPC .......... *A61N 1/3606* (2013.01); *A61N 1/36171* (2013.01); *A61N 1/0529* (2013.01); *A61N 1/0551* (2013.01)

(58) Field of Classification Search
CPC ... A61N 1/3606; A61N 1/0551; A61N 1/327; A61K 9/0009; A61K 9/0085
See application file for complete search history.

(56) References Cited

U.S. PATENT DOCUMENTS

| | | | |
|---|---|---|---|
| 6,895,280 B2 | 5/2005 | Meadows et al. | |
| 2010/0298762 A1* | 11/2010 | Thakker et al. | 604/21 |
| 2011/0106208 A1* | 5/2011 | Faltys et al. | 607/46 |
| 2012/0310140 A1* | 12/2012 | Kramer et al. | 604/20 |
| 2015/0023911 A1* | 1/2015 | Schilling et al. | 424/85.2 |

* cited by examiner

*Primary Examiner* — Robert N Wieland
(74) *Attorney, Agent, or Firm* — Faegre Baker Daniels

(57) ABSTRACT

A method of treating a patient suffering from a glioma. The method comprises delivering electrical energy to a glia at a margin of the glioma, thereby stimulating the glioma.

20 Claims, 3 Drawing Sheets

METHODS AND APPARATUS FOR TREATING GLIOMA

RELATED APPLICATION DATA

The present application claims the benefit under 35 U.S.C. §119 to U.S. provisional patent application Ser. No. 61/838,059, filed Jun. 21, 2013. The foregoing application is hereby incorporated by reference into the present application in its entirety.

TECHNICAL FIELD

The present invention relates to methods and apparatus for treating gliomas in patients.

BACKGROUND OF THE INVENTION

The central nervous system (CNS) is made up of the brain and spinal cord. Cells in the CNS normally grow in an orderly and controlled way. If for some reasons this order is disrupted, the cells continue to divide and form a tumor. A tumor is either benign or malignant. Benign tumors can continue to grow but the cells do not spread from the original site. In a malignant tumor, the cells can invade and destroy the surrounding tissue and may spread to other parts of brain and spinal cord.

Patients are diagnosed with different types of brain tumors and the most common of these tumors originate from the supporting glial cells of the brain, and are therefore, called as "gliomas." Gliomas are primary brain tumors (i.e., tumors that originate in the brain in contrast to secondary tumors that originate in a different region of the body and spread to the brain) that can be either benign or malignant. Historically, the glioma can be classified based on the type of cell from it originates, the location of glioma, and grade of the glioma.

Based on the originating cell, gliomas are divided primarily into—Astrocytoma, Ependymomas, Oligodendrocytoma, and Glioblastoma multiforme. Based on the location, gliomas can be classified according to whether they are above or below a membrane in the brain called the tentorium. The tentorium separates the cerebrum (an upper section of the brain) from the cerebellum (a lower brain section). According to an example, supratentorial is a type of glioma located above the tentorium (in the cerebrum) and infratentorial is another type of glioma that is located below the tentorium (the cerebellum).

The grade of a glioma can be determined by pathologic evaluation of the tumor. According to a grade-based classification, the glioma can be either a Low-grade or High-grade. Generally, the low-grade glioma is benign and the high-grade gliomas are malignant, and thus, carry a worse prognosis. In addition, World Health Organization (WHO) has provided a grading system for astrocytoma, which include tumors graded from I (least advanced disease—best prognosis) to IV (most advanced disease—worst prognosis).

Known procedures for treating glioma include surgery, radiation therapy, and chemotherapy, which are all subject to disadvantages. Surgery is a complicated procedure that involves a lot of risk to the patient. Radiation therapy may involve administering radiation doses to a patient over an entire year, depending on various factors such as patient age, medical condition, etc. Similarly, chemotherapy involves crossing the blood-brain barrier to allow a drug to reach a target region in the central nervous system, which can be challenging.

Thus, there exists a need for improved methods directed to providing an enhanced procedure for treating gliomas.

SUMMARY OF THE INVENTION

In accordance with the present inventions, a method of treating a patient suffering from a glioma (e.g., astrocytoma, oligodendrocytoma, and glioblastoma multiforme) is provided. The glioma may be located in the brain or in the spinal cord or within the dorsal root ganglion. The method comprises delivering electrical energy (e.g., in the range of 2 Hz to 10 KHz) to a glia at a margin of the glioma, thereby electrically stimulating the glioma and/or neural tissue surrounding the glioma. In one method, the glia lacks a neuronal input from a set of neurons due to the growth of the glioma and resulting neuronal death, in which case, the delivered electrical energy may mimic the missing neuronal input to the glial cells, thus restoring natural function of the glia. In another method, the delivered electrical energy causes at least one of a reduction in a size of the glioma and a reduction of a risk in metastasis of the glioma. In still another method, the delivered electrical energy modulates intrinsic cytokine (e.g., Leukocyte inhibitory factor (LIF), tumor necrosis factor alpha (TNF α), or interleukin) activity of the glia of the patient to modulate an inflammation response to the glioma. The delivered electrical energy may further reduce glial membrane impedance, resulting in induced current injection into the glioma and electrical modulation of glial function. An optional method comprises surgically removing at least a portion of the glioma prior to delivering the electrical energy to the glia at the margin.

Other and further aspects and features of the invention will be evident from reading the following detailed description of the preferred embodiments, which are intended to illustrate, not limit, the invention.

BRIEF DESCRIPTION OF DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present subject matter briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION

Figure 1:
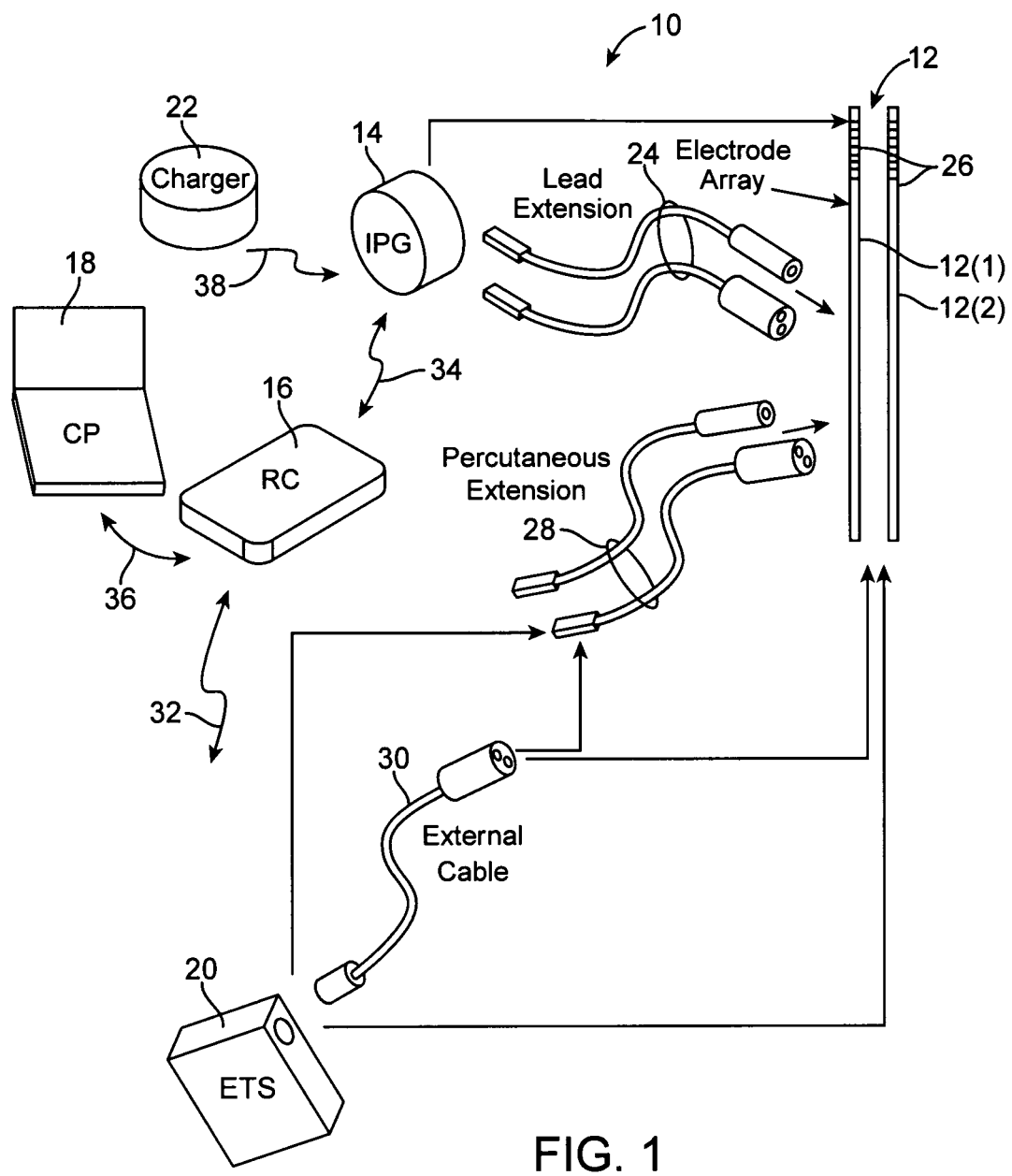
FIG. 1 is a plan view of an exemplary neurostimulation system according to an embodiment of the present invention.

Turning first to FIG. 1, an exemplary neurostimulation system 10 generally comprises a plurality of stimulation leads 12 (in this case, two), an implantable pulse generator (IPG) 14 (or alternatively RF receiver-stimulator), an external remote control (RC) 16, a Clinician's Programmer (CP) 18, an External Trial Stimulator (ETS) 20, and an external charger 22.

The IPG 14 is physically connected via one or more lead extensions 24 to the stimulation leads 12, which carry a plurality of electrodes 26 arranged in an array. The stimulation leads 12 are illustrated as percutaneous leads in FIG. 1, although as will be described in further detail below, a surgical paddle lead can be used in place of the percutaneous leads. As will also be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the neurostimulation leads 12. The ETS 20, which has similar pulse generation circuitry as the IPG 14, also delivers electrical stimulation energy in the form of a pulse electrical waveform to the electrode array 26 in accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and neurostimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18). The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For purposes of brevity, the details of the IPG 14, RC 16, CP 18, ETS 20, and external charger 22 will not be described herein. Details of exemplary embodiments of these devices are disclosed in U.S. Pat. No. 6,895,280, which is expressly incorporated herein by reference.

Significant to the present inventions, the neurostimulation system 10 can be operated to treat a glioma in a patient. Prior to treating the glioma, one or more imaging methods and devices may be employed to locate the glioma. Exemplary methods may include MRI imaging, CT scan, X-ray, etc. A biopsy may then be performed to diagnose the glioma, which involves and/or requires a minor or minimal surgery procedure to resect a certain or required portion of the glioma tissue for pathologic procedures. The biopsy, along with imaging method, is thereby used to identify whether the glioma is benign or malignant, and/or make other determinations.

Once the location of the glioma is determined, surgery may optionally be performed to excise the glioma, which is then followed by implantation of the lead(s) 12 (shown in FIG. 1) adjacent the margin of the glioma. The IPG 14 is then operated via control of the RC 16 or the CP 18 to deliver electrical stimulation energy to the lead(s) 12, thereby stimulating the margin of the excised or non-excised glioma. The delivery of electrical energy should not cause patient discomfort or significant patient discomfort. Electrical energy is provided at a suitable frequency, such as at a frequency in the range of 2 Hz-10 KHz.

The electrical energy that is provided may beneficially treat the glioma 214 in a variety of ways, including: 1) mimicking a neuronal input to the glial cells to restore the natural function of the glial cells, which had been disrupted due to the glioma, 2) reducing the size of the glioma, 3) reducing risk of metastasis of the glioma, 4) modulating an intrinsic cytokine activity of the glial cells of the patient to modulate an inflammation response to the glioma, etc. Some of the cytokines responsible for the inflammation response of glial cells and neurons are: a leukemia inhibitory factor (LIF), a tumor necrosis factor alpha (TNF $\alpha$), and/or a type of interleukin (IL). The stimulation of the glioma may reduce the glial membrane impedance, resulting in induced current injection into the glioma.

Figure 2:
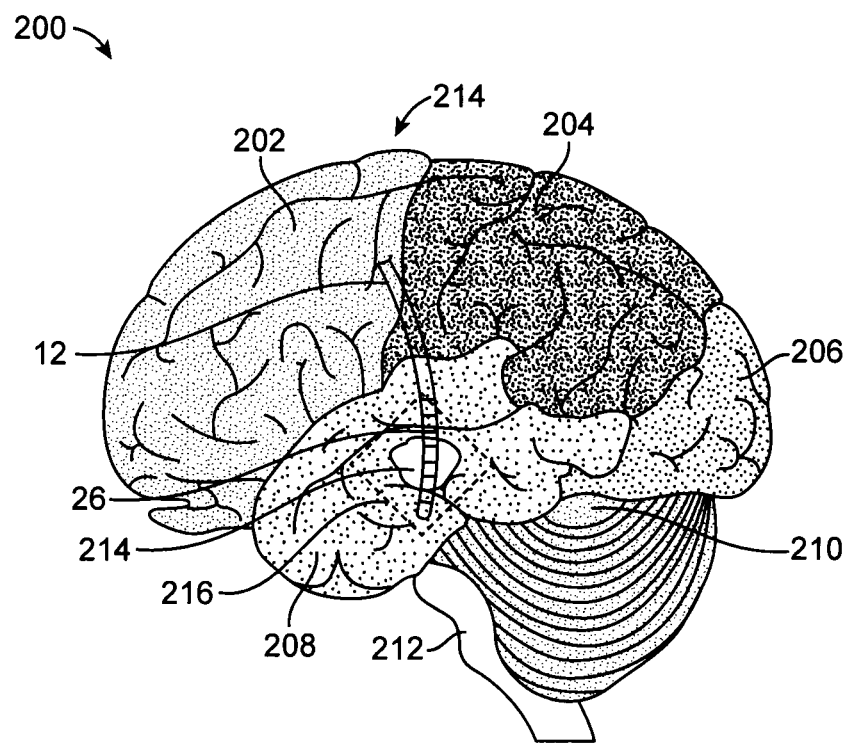
FIG. 2 is a plan view of a lead of the neurostimulation system of FIG. 1 implanted adjacent a glioma in the temporal lobe of a brain.

With reference to FIG. 2, one exemplary method of treating a glioma 214 that has developed at a location within the temporal lobe 208 of the brain 200 will now be described. The brain 200 comprises a cerebrum 214, a cerebellum 210, and a brain stem 212. The cerebrum 214, which is responsible for controlling all higher mental functions, such as thinking and memory, is divided into four lobes, including a frontal lobe 202, a parietal lobe 204, an occipital lobe 206, and a temporal lobe 208. The cerebellum 210 contributes to an autonomous balance and coordination of the human body, and the brain stem 212 plays a role in conduction, i.e., all information relayed from the spinal cord to the cerebrum 214 and cerebellum 210 and vice versa, must traverse the brain stem 212. The brain 200, along with the spinal cord, forms the central nervous system.

The brain 200 includes a number of nerve cells (i.e., neurons) that communicate with each other as well as other parts of the body, by sending messages (nerve impulses) through a system of nerve pathways or networks. Nerve cells are held in place and supported by glial cells, such as astrocytes, oligodendrocytes, and ependymal cells. In some cases, the nerve pathway(s) may be deregulated, which may result in an uncontrolled growth of glial cells, thereby forming a glioma 214. Based on the parent cell (through which the glioma 214 originates), the tumor may include ependymomas, meningiomas, astrocytomas, pituary adenomas, acoustic schwanoma (neuroma), medulloblastomas, brain stem gliomas, and optic nerve gliomas.

After locating the glioma 214 using any one of the imaging techniques described above, a trans-sulcal micro-surgical excision procedure may optionally be performed to remove the glioma 214. In accordance with this surgical procedure, an opening in the skull is formed using a drill that is operated with optical enhancements, such as X-Ray. Further, a layer of the brain, such as including dura mater, is opened under the X-Ray. A sulcus that does not include larger veins is localized and chosen. A tool, such as an arachnoid knife, is used to cut the arachnoid mater above the sulcus. Subsequently, a microscissors may be used to cut the upper arachnoid layer, such as to a distance of 3-4 cm, along the length of the sulcus. The wall of the sulcus is carefully opened using a bipolar forceps. This procedure enables entrance into the depth of the sulcus with reduced or minimal brain retraction and no (or substantially no) tissue loss. Once the bottom of the sulcus is reached, a limited resection is performed to expose the glioma 214, which is completely extirpated using bipolar forceps and an aspirator.

Once the glioma 214 is removed, the lead 12 (shown in FIG. 1) is implanted within the patient's brain 200, as shown in FIG. 2. In particular, the lead 12 is implanted adjacent a margin 216 within which the glioma 214 is located. If the glioma 214 has been surgically excised, the lead 12 may be introduced through the opening in the skull created by the surgical procedure. If the glioma 214 has not been surgically excised, and thus, a pre-existing opening in the skull has not been made, the lead 12 may be implanted using any suitable surgical procedure, such as but not limited to, introduction via a small hole (e.g., burr hole) through the skull. The hole may be a burr hole (and/or any other suitable hole), and may be created by drilling and/or by another suitable method. The hole may be formed to define a suitable diameter or size, and extend all of the way through the skull to enable the margin 126 to be easily accessed. The lead 12 may be placed within the hole, and coupled to the walls of the hole and/or the top surface of the temporal lobe 208, using a suitable burr hole fixation mechanism (not shown). Conventional stereotactic techniques may be employed in order to locate the lead 12 adjacent the margin 126. Once the lead 12 has been implanted, the hole may be covered by an appropriately sized cap (not shown), and the IPG 14 may be remotely in the patient's body (such as the abdomen or chest) and connected to the lead 12 in a conventional manner. In some cases, the IPG 14 and the lead 12 may be implanted at a site that is relatively close or adjacent to the margin 216, with the lead 12 being placed close to the margin 216.

Subsequently, the implanted SCS system 10 may be operated to deliver the stimulation energy to the margin 216 of the glioma 214, thereby treating the glioma 214 in the manner described above.

Figure 3:
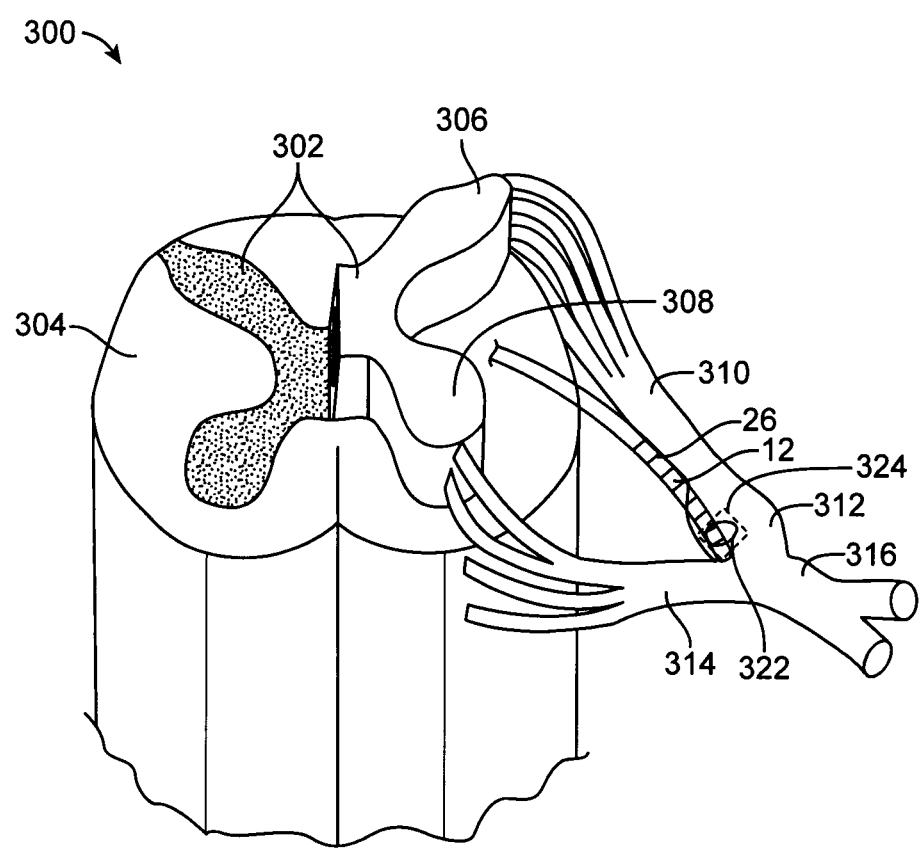
FIG. 3 is a perspective view of a lead of the neurostimulation system of FIG. 1 implanted adjacent a glioma in the dorsal root ganglion (DRG) of a spinal cord.

Although the treatment of gliomas has been specifically discussed with respect to the brain, it should be appreciated that gliomas in other regions in the central nervous system, such as the dorsal root ganglion (DRG) can be treated. For example, with reference to FIG. 3, one exemplary method of treating a glioma 322 located within the dorsal root ganglion (DRG) 312 of the spinal cord 300 will now be described.

Only certain portions of the spinal cord 300 that may be relevant to the disclosed embodiment are illustrated. The spinal cord 300 is divided into a butterfly-shaped gray matter 302 and surrounding white matter 304. The gray matter 302 is further divided into the dorsal horn 306 and the ventral horn 308.

A group of motor nerve rootlets (ventral root nerve fibers) branch off of the ventral horn 308 and combine to form the ventral root (VR) 314. Similarly, a group of sensory nerve rootlets (dorsal root (DR) nerve fibers) branch off of the dorsal horn 306 and combine to form the dorsal root 310. The dorsal root 310 and the ventral root 314 combines to form the spinal nerve 316, which innervates peripheral regions (e.g., arms, legs, etc.) of the patient's body. Symmetrical motor nerve rootlets, ventral root, sensory nerve rootlets, dorsal root, and spinal nerve are located on the opposite side of spinal cord 300, but these elements are omitted for simplicity. A number of spinal nerves branch off the spinal cord 300. In each patient, there are eight cervical spinal nerves designated C1-C8, twelve thoracic spinal nerves designated T1-T12, five lumbar spinal nerves designated L1-L5, and five sacral spinal nerves designated S1-S5.

In the same manner that the brain glioma 214 was located as described above, the glioma 322 is located and diagnosed. The glioma 322 is relatively smaller than the glioma 214 of FIG. 2. Therefore, the physician may avoid removal of the glioma 322. Once the glioma 322 is located within the dorsal root ganglion 312 and diagnosed, the lead 12 (shown in FIG. 1) is implanted adjacent the margin 324 of the dorsal root ganglion 312. The lead 12 may be implanted adjacent the dorsal root ganglion (DRG) 312 either epidurally or surgically in a conventional manner.

Once the lead 12 is implanted adjacent the DRG 312, the IPG 14 may be remotely in the patient's body (such as the abdomen or chest) and connected to the lead 12 in a conventional manner. Subsequently, the implanted SCS system 10 may be operated to deliver the stimulation energy to the margin 324 of the glioma 322, thereby treating the glioma 322 in the manner described above.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present invention. Thus, the present inventions are intended to cover alternatives, modifications, and equivalents, which may be included within the spirit and scope of the present inventions as defined by the claims.

What is claimed is:

1. A method of treating a patient suffering from a glioma, the method comprising:

delivering electrical energy to a glia at a margin of the glioma, thereby stimulating the glioma and/or neural tissue surrounding the glioma and causing a reduction in a size of the glioma.

2. The method of claim 1, wherein the frequency of the delivered electrical energy is in the range of 2 Hz to 10 KHz.

3. The method of claim 1, wherein the glia lacks a neuronal input from a set of neurons due to the growth of the glioma, and the delivered electrical energy mimics a neuronal input to the glia to restore a natural functioning of the glia.

4. The method of claim 1, wherein the delivered electrical energy modulates an intrinsic cytokine activity of the glia of the patient to modulate an inflammation response to the glioma.

5. The method of claim 4, wherein the cytokine is at least one of a Leukocyte inhibitory factor (LIF), tumor necrosis factor alpha (TNF a), and interleukin.

6. The method of claim 1, wherein the delivered electrical energy reduces a glial membrane impedance, resulting in induced current injection into the glioma.

7. The method of claim 1, further comprising surgically removing at least a portion of the glioma prior to delivering the electrical energy to the glia at the margin.

8. The method of claim 1, wherein the glioma is located in the brain of the patient.

9. The method of claim 1, wherein the glioma is one of an astrocytoma, oligodendrocytoma, and glioblastoma multiforme.

10. The method of claim 1, wherein the glioma is located on a dorsal root ganglion (DRG) of the patient.

11. A method of treating a patient suffering from a glioma, the method comprising:

delivering electrical energy to a glia at a margin of the glioma, thereby stimulating the glioma and/or neural tissue surrounding the glioma and causing a reduction of a risk in metastasis of the glioma.

12. The method of claim 11, wherein the delivered electrical energy modulates an intrinsic cytokine activity of the glia of the patient to modulate an inflammation response to the glioma.

13. The method of claim 12, wherein the cytokine is at least one of a Leukocyte inhibitory factor (LIF), tumor necrosis factor alpha (TNF a), and interleukin.

14. The method of claim 11, wherein the delivered electrical energy reduces a glial membrane impedance, resulting in induced current injection into the glioma.

15. The method of claim 11, further comprising surgically removing at least a portion of the glioma prior to delivering the electrical energy to the glia at the margin.

16. The method of claim 11, wherein the glioma is located in the brain of the patient.

17. The method of claim 11, wherein the glioma is one of an astrocytoma, oligodendrocytoma, and glioblastoma multiforme.

18. The method of claim 11, wherein the glioma is located on a dorsal root ganglion (DRG) of the patient.

19. The method of claim 11, wherein the frequency of the delivered electrical energy is in the range of 2 Hz to 10 KHz.

20. The method of claim 11, wherein the glia lacks a neuronal input from a set of neurons due to the growth of the glioma, and the delivered electrical energy mimics a neuronal input to the glia to restore a natural functioning of the glia.

* * * * *